United States Patent
Mirov et al.

(10) Patent No.: US 11,185,636 B2
(45) Date of Patent: Nov. 30, 2021

(54) ELECTROSTATIC ROTARY ENCODER

(71) Applicant: Verily Life Sciences LLC, South San Francisco, CA (US)

(72) Inventors: Russell Mirov, Los Altos, CA (US); Benjamin Krasnow, Redwood City, CA (US)

(73) Assignee: Verily Life Sciences LLC

( * ) Notice: Subject to any disclaimer, the term of this patent is extended or adjusted under 35 U.S.C. 154(b) by 50 days.

(21) Appl. No.: 16/513,618

(22) Filed: Jul. 16, 2019

(65) Prior Publication Data
US 2020/0030543 A1 Jan. 30, 2020

Related U.S. Application Data

(60) Provisional application No. 62/703,665, filed on Jul. 26, 2018.

(51) Int. Cl.
*G01R 27/26* (2006.01)
*A61M 5/315* (2006.01)
*G01D 5/241* (2006.01)

(52) U.S. Cl.
CPC ....... *A61M 5/31553* (2013.01); *G01D 5/2412* (2013.01); *A61M 2205/3317* (2013.01); *A61M 2205/3569* (2013.01)

(58) Field of Classification Search
CPC .......... G01D 5/145; G01D 5/147; G01D 5/24; G01D 5/2412; G01D 5/2415; G01D 5/2451
See application file for complete search history.

(56) References Cited

U.S. PATENT DOCUMENTS

| | | | | |
|---|---|---|---|---|
| 4,156,566 A | * | 5/1979 | Thiele | G03B 17/18 307/400 |
| 4,441,038 A | * | 4/1984 | Tanaka | H01G 7/02 307/400 |

(Continued)

FOREIGN PATENT DOCUMENTS

| CA | 2200106 | 4/1991 |
|---|---|---|
| EP | 3132821 A1 | 2/2017 |

(Continued)

OTHER PUBLICATIONS

"Rotary encoder," Wikipedia, The Free Encyclopedia, Jan. 16, 2018, <https://en.wikipedia.org/wiki/Rotary_encoder> [retrieved Feb. 1, 2018], 6 pages.

(Continued)

*Primary Examiner* — Thang X Le
(74) *Attorney, Agent, or Firm* — Christensen O'Connor Johnson Kindness PLLC

(57) ABSTRACT

A rotary encoder includes an electret unit, an electrostatic field sensor, and a controller. The electret unit generates an electrostatic field. The electrostatic field sensor is disposed proximate to the electret unit to sense a modulation of the electrostatic field that varies with rotation of one or more rotary components of the rotary encoder about a rotation axis of the rotary encoder. The controller is electrically coupled to the electrostatic field sensor to track activations of the electrostatic field sensor as the one or more rotary components rotate. The controller is configured to digitally encode a rotational position of the one or more rotary components based upon the activations.

22 Claims, 8 Drawing Sheets

(56) References Cited

U.S. PATENT DOCUMENTS

| | | | |
|---|---|---|---|
| 5,311,666 A * | 5/1994 | Jacobsen | G01D 5/2415 33/1 N |
| 5,394,070 A * | 2/1995 | Jacobsen | G01B 7/003 200/11 R |
| 5,565,717 A * | 10/1996 | Lewiner | H01G 7/02 264/436 |
| 6,277,099 B1 | 8/2001 | Strowe et al. | |
| 6,585,698 B1 | 7/2003 | Packman et al. | |
| 6,608,483 B1 * | 8/2003 | Hill | G01R 29/12 324/457 |
| 7,008,399 B2 | 3/2006 | Larsen et al. | |
| 7,126,495 B2 * | 10/2006 | Netzer | G01D 11/245 340/870.39 |
| 8,632,509 B2 | 1/2014 | Møller et al. | |
| 9,435,666 B2 | 9/2016 | Richter | |
| 9,522,238 B2 | 12/2016 | Nielsen et al. | |
| 9,634,153 B2 | 4/2017 | Moon et al. | |
| 2004/0007877 A1 * | 1/2004 | Boland | H02N 1/08 290/1 R |
| 2010/0045489 A1 * | 2/2010 | Gondo | H03M 1/485 341/15 |
| 2011/0062968 A1 * | 3/2011 | Renno | G01R 29/12 324/654 |
| 2015/0115331 A1 * | 4/2015 | Moon | H01L 29/84 257/254 |
| 2016/0015903 A1 | 1/2016 | Madsen et al. | |

FOREIGN PATENT DOCUMENTS

| | | |
|---|---|---|
| JP | S5757211 A | 4/1982 |
| JP | 2015-152513 A | 8/2015 |
| JP | 2016046837 A | 4/2016 |
| WO | 2012046199 A1 | 4/2012 |
| WO | 2013/120778 A1 | 8/2013 |
| WO | 2016198516 A1 | 12/2016 |

OTHER PUBLICATIONS

International Search Report and Written Opinion for corresponding International Application PCT/US2019/042658, dated Sep. 18, 2019, 14 pages.

* cited by examiner

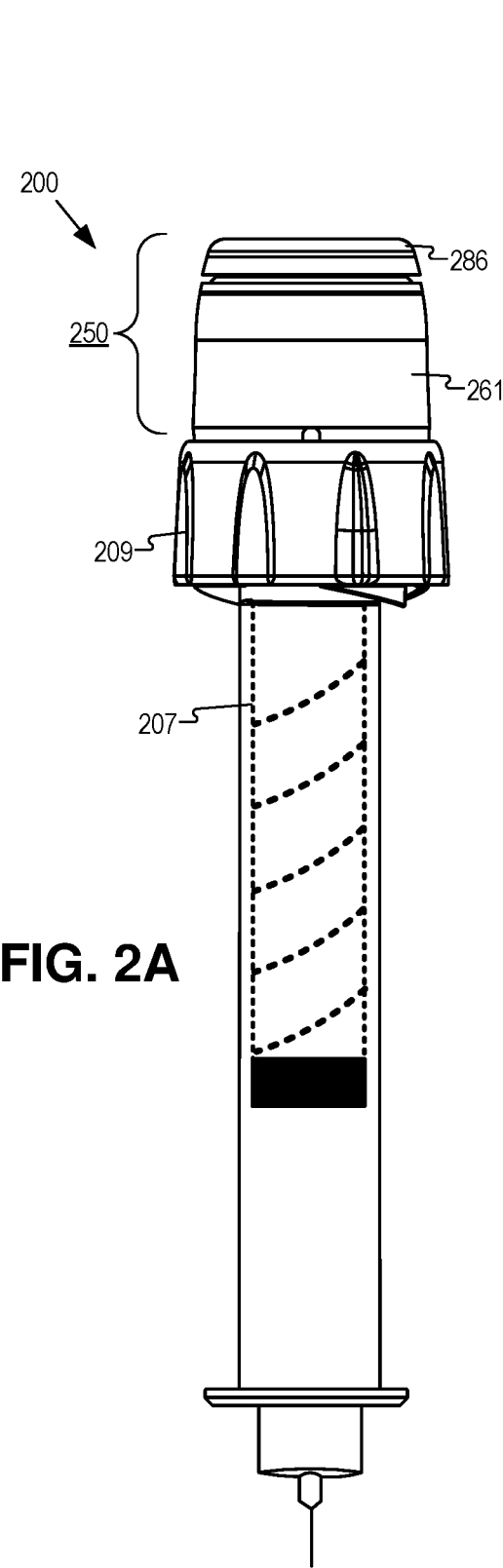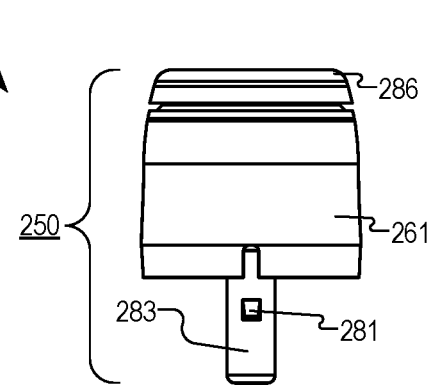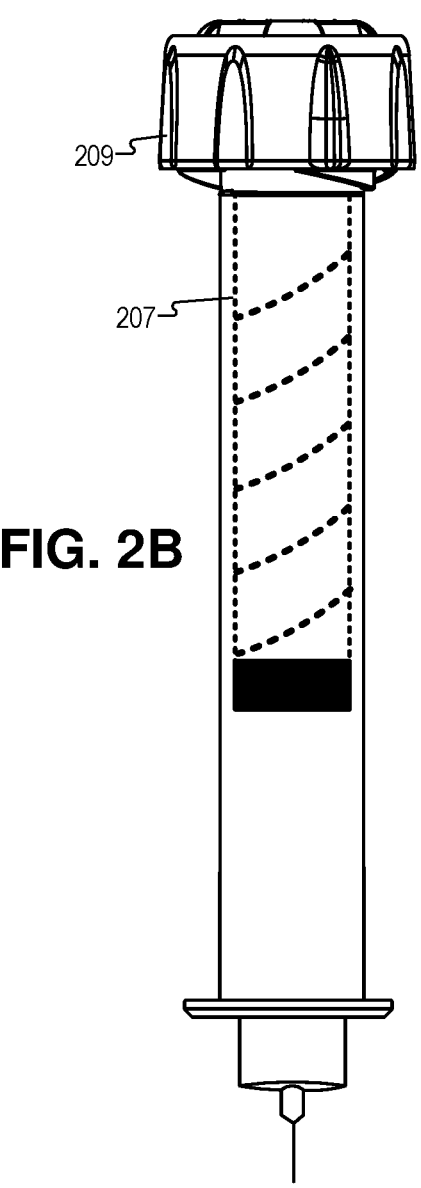
FIG. 2A
FIG. 2B

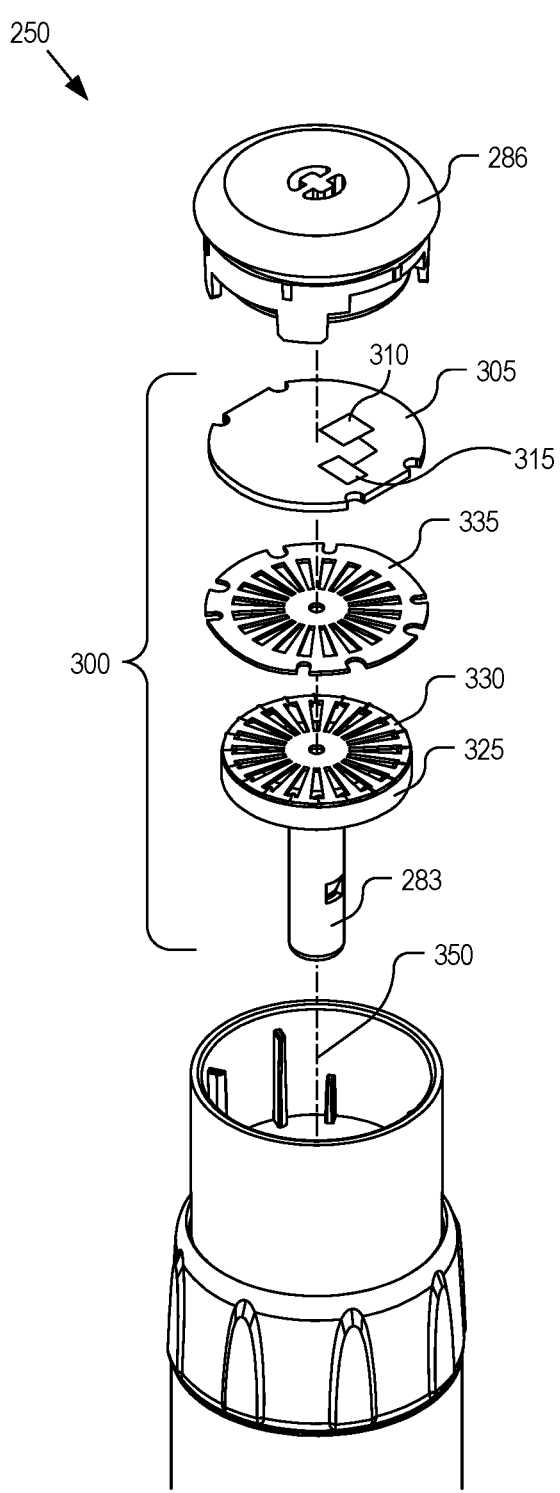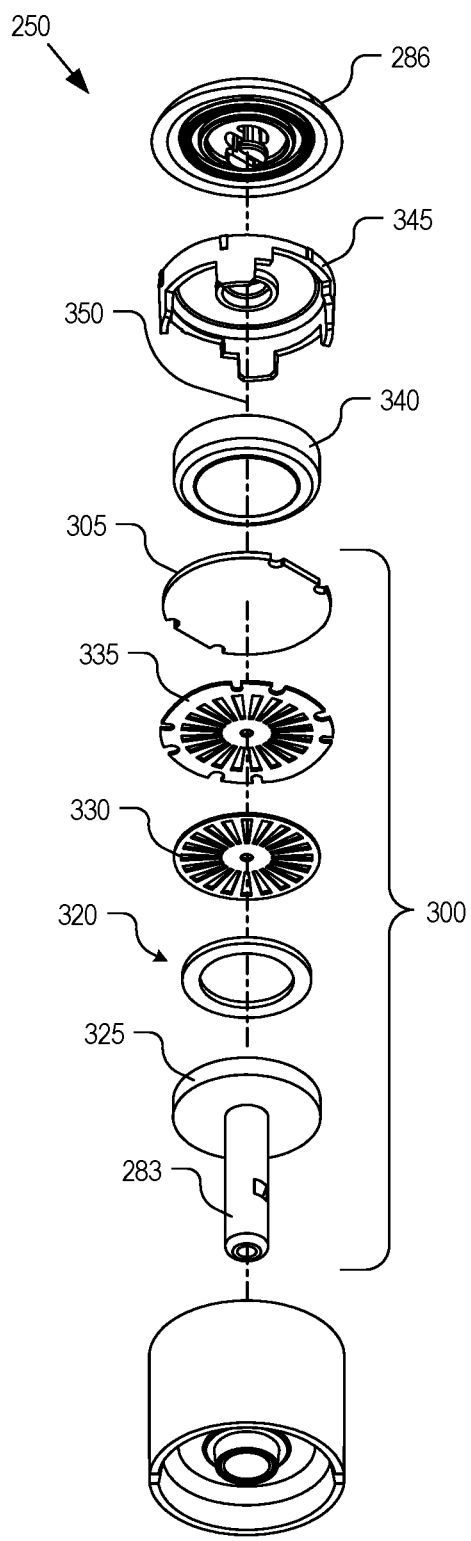
FIG. 3A   FIG. 3B

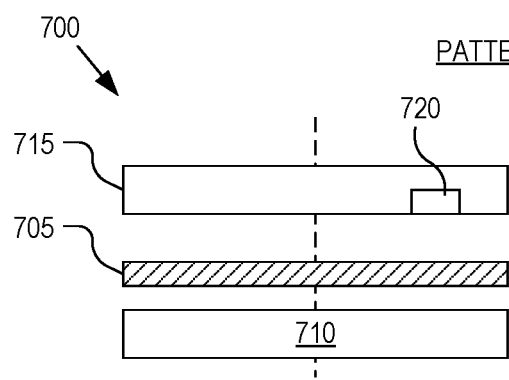
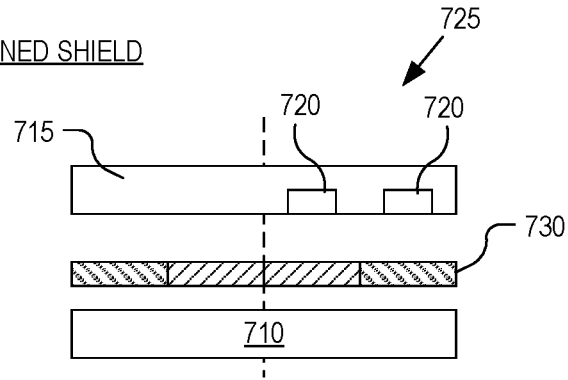
FIG. 7A  FIG. 7B
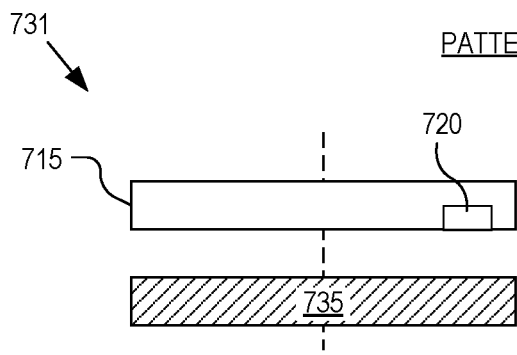
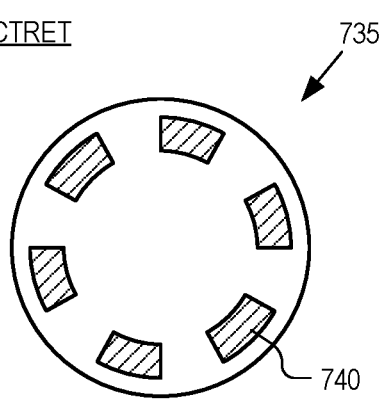
FIG. 7C
FIG. 7D
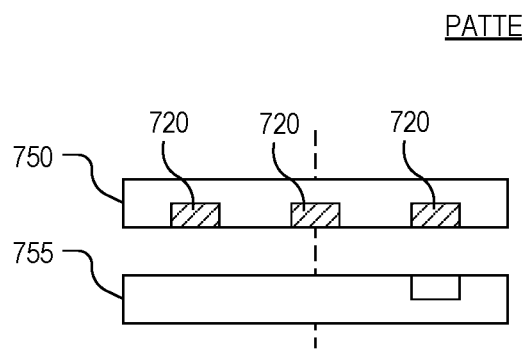
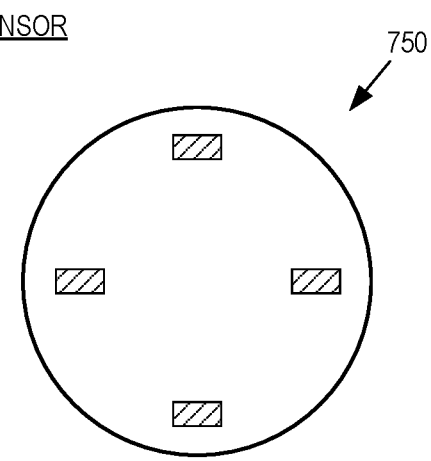
FIG. 7E
FIG. 7F

ELECTROSTATIC ROTARY ENCODER

CROSS-REFERENCE TO RELATED APPLICATIONS

This application claims the benefit of U.S. Application No. 62/703,665, filed on Jul. 26, 2018, the contents of which are incorporated herein by reference.

TECHNICAL FIELD

This disclosure relates generally to rotary encoders, and in particular but not exclusively, relates to dosage-tracking of a drug injection pen using a rotary encoder.

BACKGROUND INFORMATION

A rotary encoder is a device that converts an angular position or rotational motion of a shaft to a signal, which may be used to track the angular position or rotational motion of the shaft. Rotary encoders can be classified into two subcategories: absolute rotary encoders and relative rotary encoders. Absolute rotary encoders identify the absolute angular position of the shaft at a given moment while relative rotary encoders identify the motion of the shaft, which can be tracked to calculate the absolute angular position relative to a starting position. A relative rotary encoder uses an extraneous counter to maintain state information in order to compute the absolute angular position of the shaft. Rotary encoders sometimes use multiple "tracks" to increase the resolution for encoding angular position or rotational motion of the shaft. Tracks are often implemented as a "ring pattern" on the shaft and the technique may also be referred to as "quadrature encoding."

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

FIG. 2A illustrates a drug injection pen that includes a dosage measurement system using an electrostatic rotary encoder, in accordance with an embodiment of the disclosure.

FIG. 2B illustrates the drug injection pen with a pen button housing that incorporates the electrostatic rotary encoder separated from the delivery mechanism housing, in accordance with an embodiment of the disclosure.

FIGS. 3A & 3B are exploded view illustrations of the pen button housing including the electrostatic rotary encoder, in accordance with an embodiment of the disclosure.

FIG. 7A is a cross-sectional illustration of an electrostatic rotary encoder that includes a patterned electrostatic shield, in accordance with an embodiment of the disclosure.

FIG. 7B is a cross-sectional illustration of a quadrature electrostatic rotary encoder that includes a patterned electrostatic shield, in accordance with an embodiment of the disclosure.

FIG. 7C is a cross-sectional illustration of an electrostatic rotary encoder that includes a patterned electret unit, in accordance with an embodiment of the disclosure.

FIG. 7D is a plan view illustration of a patterned electret unit, in accordance with an embodiment of the disclosure.

FIG. 7E is a cross-sectional illustration of an electrostatic rotary encoder that includes a patterned electrostatic field sensor, in accordance with an embodiment of the disclosure.

FIG. 7F is a plan view illustration of a patterned electrostatic field sensor, in accordance with an embodiment of the disclosure.

DETAILED DESCRIPTION

Figure 1:
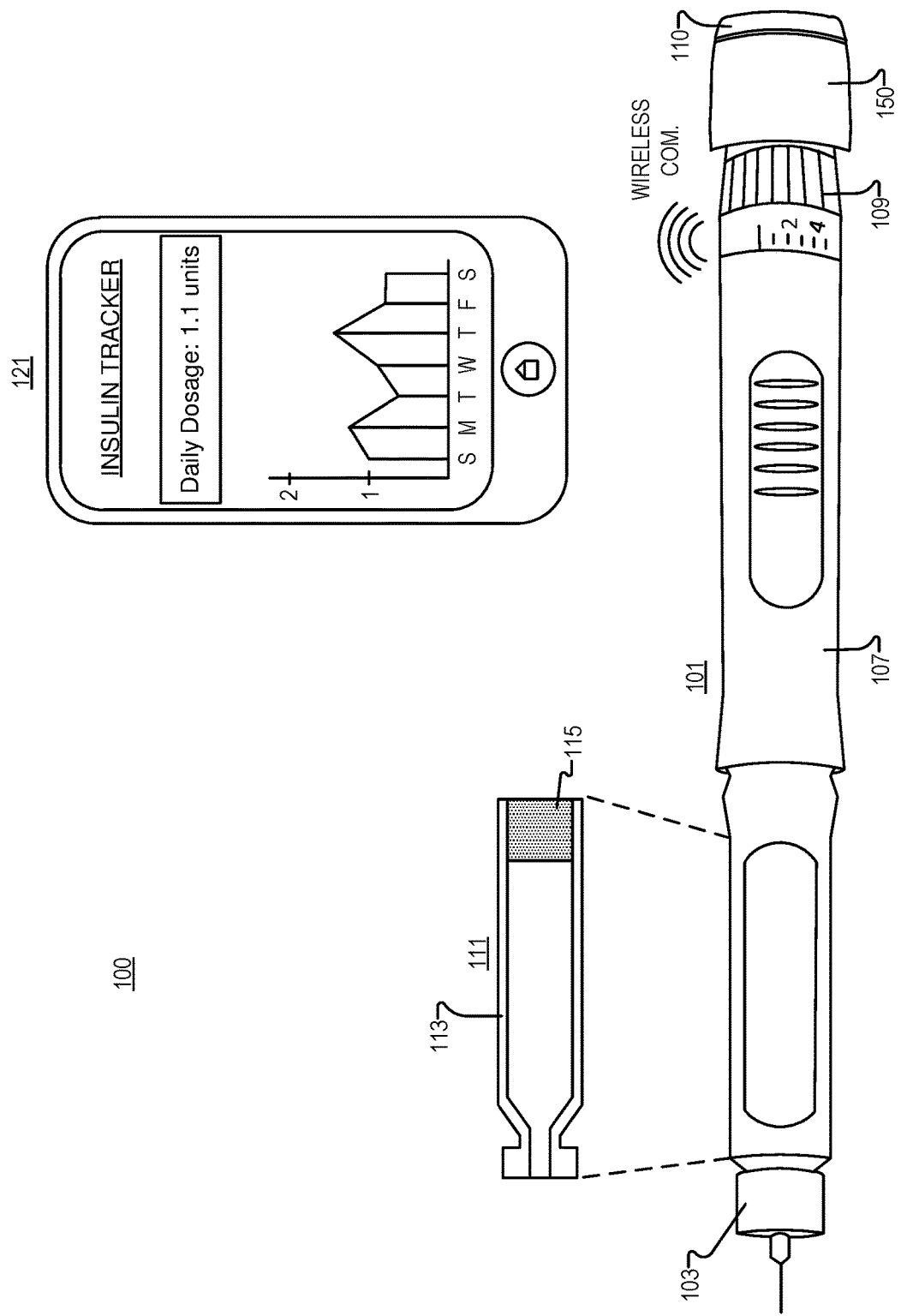
FIG. 1 illustrates a drug injection system, in accordance with an embodiment of the disclosure.

Embodiments of a system, apparatus, and method of operation for an electrostatic rotary encoder are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Measuring the quantity and recording the timing of a drug's administration is an integral part of many disease treatments. For many treatments, to achieve the best therapeutic effect, specific quantities of a drug may need to be injected at specific times of day. For example, individuals suffering from diabetes may be required to inject themselves regularly throughout the day in response to measurements of their blood glucose. The frequency and volume of insulin injections should be carefully tracked and controlled to keep the patient's blood glucose level within a healthy range.

Currently, there are a limited number of methods or devices capable of tracking drug administration without requiring the user to manually measure and record the volume, date, and time. A variety of glucose injection syringes/pens have been developed, but there is much room for significant advancement in the technology in order to reduce the size, lower the cost, enhance the functionality, and improve the accuracy. Thus, the current technology may not be an ideal long-term solution. For example, current insulin pens are often disposable, but do not include dosage tracking functionality. A smaller portion of the market is composed of reusable pens which are more expensive.

Pharmaceutical dose delivery tracking (of a drug injection pen) often requires quantifying the motion or position of delivery mechanism components. This may require translating a linear motion/position of the plunger head that forces a drug out of a container (e.g., drug vial) to a rotational motion, which is encoded for drug delivery tracking purposes. Embodiments of the electrostatic rotary encoder described herein are well suited for accurately tracking dispensed dosages of a drug from an injectable pen. However, it should be appreciated that the electrostatic rotary encoders described herein are not limited for use with just dosage tracking systems of a. drug injection apparatus, but rather may be broadly applicable to any device that may benefit from inclusion of a rotary encoder, particularly a low power rotary encoder.

The below describe techniques of detecting and encoding rotational motion, track the movement/rotation/proximity of a statically charged element called an electret. Operation of electret elements are understood in their common application of microphones. In a microphone application, the vibration of a thin electret film modulates the charge at the gate of an amplifier converting sound pressure levels into an electronic signal that represents the audio signal. In this rotary encoder application the electret element provides a large fixed charge that can be physically repositioned or blocked to detect motion. Since the described embodiments do not use bias fields or alternating current (AC) probe signals like capacitive sensors, the electrostatic rotary encoders described herein represent low power solutions compared to alternative capacitive solutions.

The embodiments described herein utilize an electret unit in conjunction with an electrostatic field sensor to detect relative rotary motion or a change in electrostatic field strength/polarity. In one embodiment, the electret unit, which includes at least one electret element, and the electrostatic field sensor can be in motion relative to each other (i.e., one or both elements in motion). In one embodiment, the electret unit and the electrostatic field sensor can have fixed positions relative to each other while an electrostatic shield (e.g., shutter) can alter the electrostatic field in response to a rotary motion. In all of these embodiments, a rotational modulation pattern is generated using an electret unit and related to rotation of one or more rotary components of the rotary encoder. The electrostatic rotary encoder works with or without direct physical contact, across an air gap, or through an insulating barrier. The electret unit can have a relatively simple and uniform charge distribution (e.g., a monolithic electret element), or it can have a charge distribution pattern, including a set of complex charge patterns such as charged stripes, poles, sectors, etc.

FIG. 1 illustrates a drug injection system 100, in accordance with an embodiment of the disclosure. Drug injection system 100 includes injection pen 101, drug cartridge 111, and processing device 121 (e.g., a portable computing device, a smart phone, etc.).

Drug cartridge 111 includes cartridge body 113 and plunger head 115. In the depicted embodiment, plunger head 115 starts near the rear of drug cartridge 111 and is pushed forward in drug cartridge 111 by a dosage injection mechanism disposed in injection pen 101. This forces medication/fluid out of the narrow end of drug cartridge 111 when a user chooses to dispense a fluid.

Injection pen 101 is a hand-held device and includes needle 103, body/housing 107 (including a dosage injection mechanism to push in plunger head 115 and expel fluid from drug cartridge 111), drug delivery control wheel 109 (twist wheel or dial 109 to "click" select the dosage), and pen button 150 (which includes push button 110 to dispense the selected quantity of the fluid from cartridge 111). In one embodiment, pen button 150 includes a dosage measurement system. As shown, housing 107 is configured to accept cartridge 111. In one embodiment, cartridge 111 may be disposed in an insert which screws/snaps onto the bulk of housing 107. However, as one of ordinary skill in the art will appreciate, injection pen 101 can assume other configurations and have other components.

As stated, injection pen 101 includes a housing/body 107 shaped to accept a cartridge containing a fluid, and also includes a dosage injection mechanism positioned in the housing 107 to produce a rotational motion and force the fluid out of the cartridge when the drug injection pen 101 dispenses the fluid. A dosage measurement system is also disposed in the pen (e.g., in button 150 or elsewhere in pen body 107) to track the rotational motion of the dosage injection mechanism. The dosage measurement system encodes the rotational motion of the dosage injection mechanism to track the amount of fluid dispensed and further outputs a signal indicative of the rotation or fluid dispensed.

A controller is also disposed in drug injection pen 101, as part of the dosage measurement system. The controller includes logic that when executed by the controller causes the controller to record the electrical signals indicative of the fluid dispensed into a dispensing log. One of ordinary skill in the art will appreciate that the controller may be static (e.g., have logic in hardware), or dynamic (e.g., have programmable memory that can receive updates in the form of software or firmware instructions). In some embodiments, the controller may register the electrical signal output from the dosage measurement system as an injection event of the fluid, and the controller may calculate a quantity of the fluid dispensed based, at least in part, on a number of the injection events of the fluid registered by the controller. It is appreciated that this circuitry, which will be described in greater detail in connection with other figures, may be disposed anywhere in drug injection pen 101 (e.g., in body/housing 107 or pen button 150), and in some instances, logic may be distributed across multiple devices.

Processing device 121 (e.g., a smartphone, tablet, general purpose computer, distributed system, servers connect to the internet, or the like) may be coupled to receive dosage data from injection pen 101 to store/analyze this data. For instance, in the depicted embodiment, processing device 121 is a smartphone, and the smartphone has an application running recording how much insulin has been dispensed from injection pen 101. In the illustrated embodiment, the application plots how much insulin has been injected by the user over a historical period of time (e.g., week). In this embodiment, a power source is electrically coupled to the controller in injection pen 101, and a transceiver is electrically coupled to the controller to send and receive data to/from processing device 121. Here, data includes information indicative of a quantity of the fluid dispensed. Transceiver may include Bluetooth, RFID, or other wireless communications technologies.

FIGS. 2A and 2B illustrate a pen housing 207 and pen button 250 of a drug injection pen 200, in accordance with an embodiment of the disclosure. Pen button 250 includes a dosage measurement system while pen housing 207 houses the delivery or injection mechanism. Drug injection pen 200 is one possible implementation of injection pen 100 illustrated in FIG. 1. As shown, pen button 250 is fabricated to be inserted into the back end of injection pen 200 (opposite the dispensing end). Pen button 250 includes a pair of notches 281, cut into a shaft/column 283 protruding from pen button 250, which clip into a rotating delivery mechanism (e.g., corkscrew gear) within pen housing 207. It is appreciated that the pen button housing 261 contains the dosage measurement system including electronics to measure a rotational motion of shaft 283 of the dosage injection mechanism. In other words, notches 281 of shaft 283 lock or "snap" into the dosage delivery mechanism so that pen button 250 experiences relative rotation when the pen is dispensing a dose of fluid. In the depicted embodiment, pen button 250 rotates along with drug delivery control wheel 209 when the pen is dispensing a dose. So that the user's thumb does not interfere with this rotation, a spinner 286 are disposed on a top side of pen button 250. Thus rotary components of pen button 250 spin when the injection pen dispenses fluid, but the user's thumb and fingers do not prevent dispensing of the fluid. In other words, rotary components of pen button 250 (e.g., the sides of the button housing 261) are coupled to rotate around a rotation axis (e.g., longitudinal axis of the drug injection pen) while other components remain stationary (e.g., pen housing 207).

Figure 4:
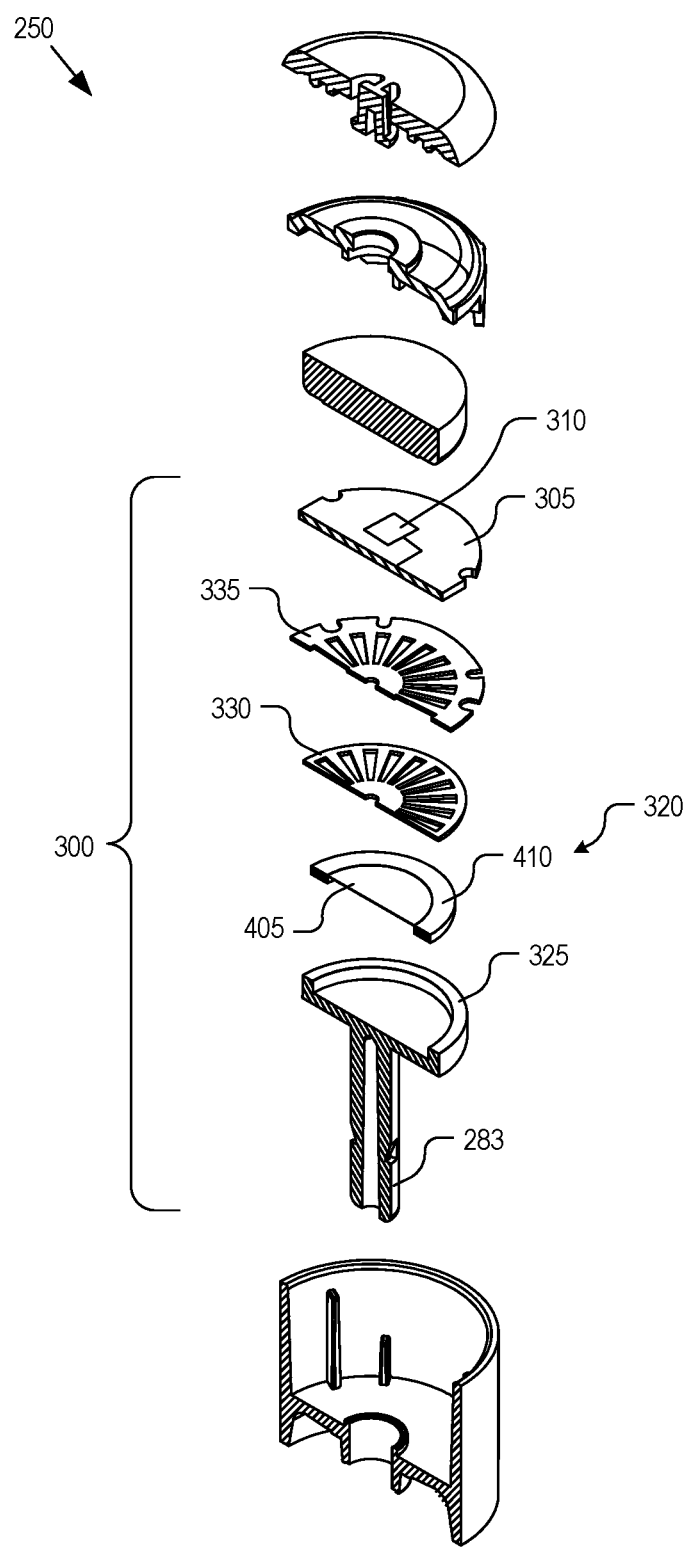
FIG. 4 is an exploded view cross-sectional illustration of the pen button housing including the electrostatic rotary encoder, in accordance with an embodiment of the disclosure.

FIGS. 3A, 3B, and 4 illustrate exploded views of pen button 250 of FIGS. 2A and 2B, in accordance with an embodiment of the disclosure. As shown, pen button 250 includes a number of components of a dosage measurement system that are stacked in a layered configuration in pen button 250. The dosage measurement system tracks a delivered dosage of a drug by tracking the rotational motion of internal rotary components using electrostatic rotary encoder 300. Electrostatic rotary encoder 300 tracks the relative rotation of the internal rotary components of drug injection pen 200, which correlates to the delivered dosage of a fluid from a vial. Electrostatic rotary encoder 300 is described in connection with drug injection pen 200; however, it should be appreciated that electrostatic rotary encoder 300 may be used with a variety of different types of drug injection pens, and furthermore, may be implemented in any device where it is desired to have a low power solution for tracking or measuring a rotational motion between two components.

FIGS. 3A and 3B illustrate exploded view illustrations of rotary encoder 300 with FIG. 3A illustrating a partial assembly and FIG. 3B illustrating a complete disassembled exploded view. FIG. 4 is a cross-sectional exploded view of rotary encoder 300 to illustrate further details that are not readily seen in the views of FIGS. 3A and 3B. The illustrated embodiment of rotary encoder 300 includes a circuit board 305, upon which a controller 310 and an electrostatic field sensor 315 are disposed, an electrostatic shield, an electret unit 320, a support member 325, and a shaft 283. The illustrated embodiment of the electrostatic shield includes a first shield layer 330 and a second shield layer 335. The illustrated pen button 250 further includes a battery 340 and battery housing 345 to which spinner 286 mounts via a thrust bearing.

Electrostatic rotary encoder 300 operates by modulating the electrostatic field generated by electret unit 320 as sensed by electrostatic field sensor 315. The modulation is directly related to the rotational motion/position of rotary components of rotary encoder 300. In the illustrated embodiment, these components include shaft 283, which is coupled to the fluid delivery mechanism of drug injection pen 200 and thus related by extension to the dosages of fluids dispensed. The modulation of the electrostatic field causes electrostatic field sensor 315 to reciprocally activate and deactivate. These activations are tracked by controller 310, which digitally encodes the rotational/angular position of shaft 283 via the activations. As mentioned, the activations, and by extension the rotational position of shaft 283, are related to the volume of fluid dispensed by drug injection pen 200.

The modulation of the electrostatic field at electrostatic field sensor 315 may be achieved via a number of techniques. In the illustrated embodiment of FIGS. 3A, 3B, and 4, the modulation is achieved by rotating an intervening electrostatic shield to periodically block or interfere with (e.g., modulate) the electrostatic field generated by electret unit 320. In another embodiment, the electret unit itself is patterned and either (or both) the electret unit or the electrostatic field sensor is rotated (discussed in greater detail in connection with FIGS. 7C and 7D). In yet another embodiment, the electrostatic field sensor is patterned and either (or both) the electret unit or the electrostatic field sensor is rotated (discussed in greater detail in connection with FIGS. 7E and 7F). However, it should be appreciated that any of the configurations described herein may be used in rotary encoder 300. It is further contemplated that combinations of these configurations may be used together in a single embodiment to achieve modulation of the electrostatic field. Multiple components including one or more of the electret unit, the electrostatic shield, or the electrostatic field sensor may rotate.

Referring to FIG. 4, electret unit 320 inserts into a recess of support member 325, which holds electret unit 320 in place. In the illustrated embodiment, electret unit 320 includes a monolithic electret element 405 disposed in the center of a conductive annular substrate 410. In one embodiment, the monolithic electret element 405 is a puck having a uniform static charge or simple dipole charge distribution. Monolithic electret element 405 is surrounded by annular substrate 410. Since annular substrate 410 is conductive (e.g., copper, aluminum, other metals, etc.), its conductive nature forms a sort of perimeter cage that blocks external electromagnetic/electrostatic interference. In one embodiment, annular substrate 410 is wrapped or coated in a dielectric membrane in or on which monolithic electret element 405 is disposed. Further as illustrated, first shield layer 330 is attached over support member 325 with electret unit 320 sandwiched there between.

Figure 5B:
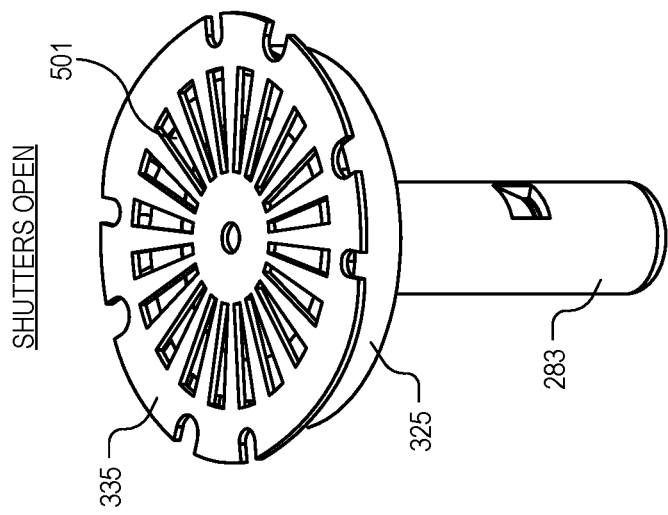
FIGS. 5A & 5B are perspective view illustrations of an electrostatic shield having shutters in a closed and open position, in accordance with an embodiment of the disclosure.
Figure 5A:
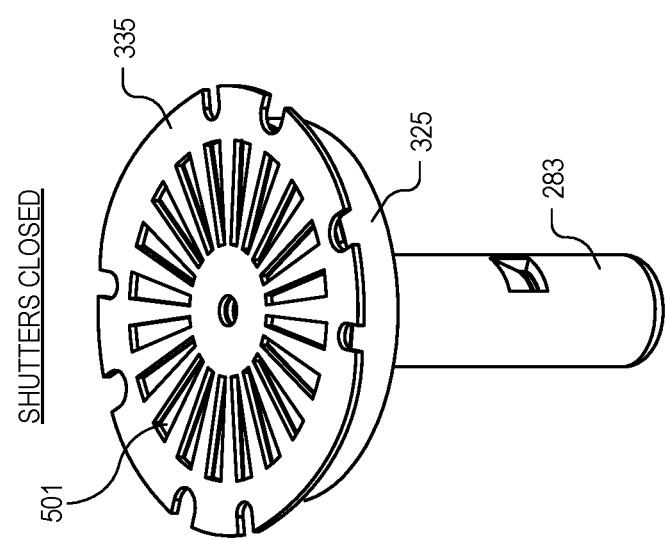

During operation, the fluid delivery mechanism of drug injection pen 200 translates the linear plunging motion that dispenses the fluid into a rotational motion. Shaft 283 is coupled to the fluid delivery mechanism via notch 281 and rotates in unison with the dose dispensing. Support member 325, which is connected to shaft 283, rotates first shield layer 330. In the illustrated embodiment, shaft 283 is a rotary component of rotary encoder 300 that drives the rotation of the other rotary components including first shield layer 330. In the illustrated embodiment, second shield layer 335 includes notches around its perimeter, which hold it stationary while shaft 283 spins about rotation axis 350. As the two layers of the electrostatic shield rotate relative to each other, their hole patterns form shutters that periodically open and close based upon their relative rotational/angular positions. FIG. 5A illustrates shutters 501 in a closed position while FIG. 5B illustrates shutters 501 in the open position. The opening and closing of shutters 501 modulates the electrostatic field generated by electret unit 320 and sensed at electrostatic field sensor 315 disposed on substrate 305.

Figure 6A:
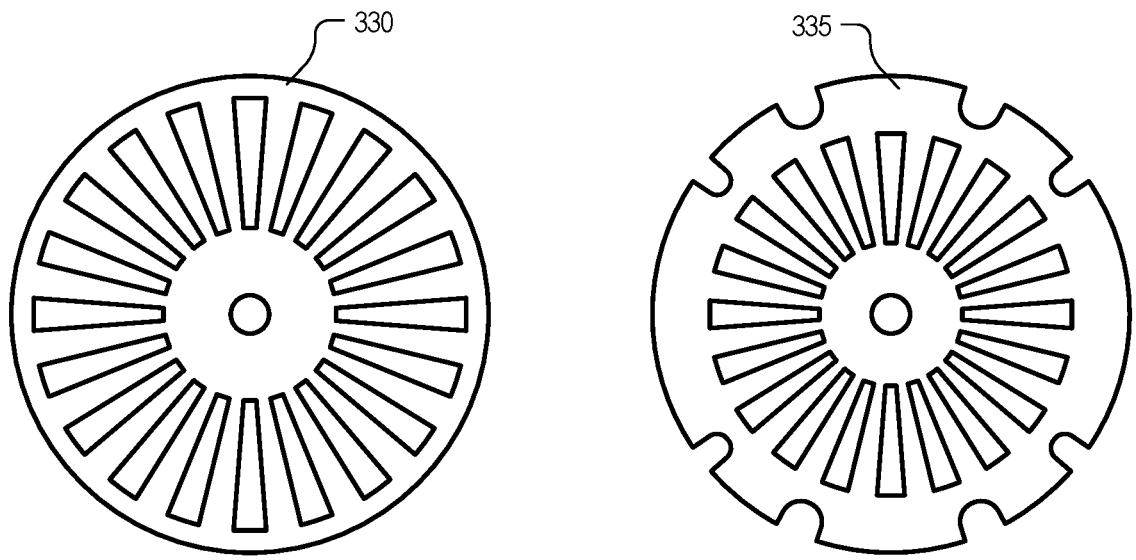
FIG. 6A illustrates layers of an electrostatic shield, in accordance with an embodiment of the disclosure.
Figure 6B:
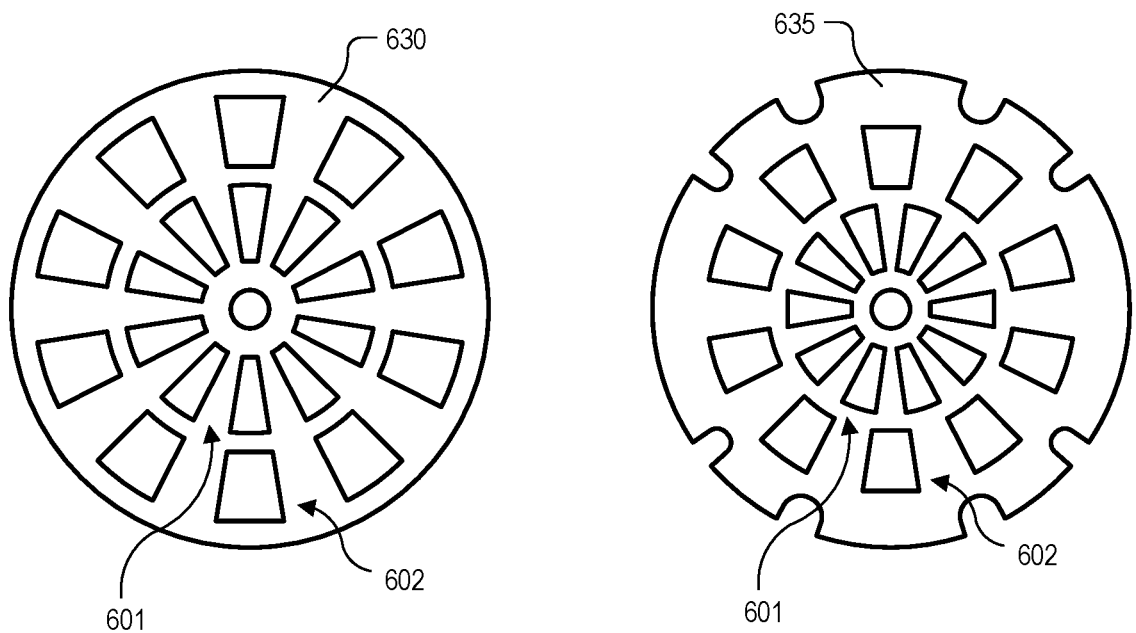
FIG. 6B illustrates layers of an electrostatic shield for quadrature encoding, in accordance with an embodiment of the disclosure.

FIGS. 6A and 6B illustrate example configurations for shield layers 330 and 335 of the electrostatic shield. FIG. 6A illustrates shield layers 330 and 335, which each include a single track hole pattern. FIG. 6B illustrates shield layers 630 and 635 which each include a dual track hole pattern. The dual track pattern includes an inner ring pattern 601 and an outer ring pattern 602 of holes to provide quadrature encoding.

FIGS. 7A-7F illustrate various configurations of the electret unit, electrostatic shield, and/or electrostatic field sensor that may be used separately or jointly with each other in electrostatic rotary encoder 300. FIG. 7A is a cross-sectional illustration of an electrostatic rotary encoder configuration 700 that includes a patterned electrostatic shield 705 disposed between a monolithic electret element 710 and an electrostatic field sensor 715. Configuration 700 is similar as illustrated in FIGS. 3-4 and operates by rotating electrostatic shield 705 (or a subcomponent thereof) to modulate the electrostatic field at electrostatic field sensor 715. Although FIG. 7A illustrates electrostatic field sensor 715 implemented with a single sensing circuit 720, it should be appreciated that electrostatic field sensor 715 may be implemented with multiple sensor circuits 720 evenly distributed over electrostatic shield 705. FIG. 7B illustrates a quadrature electrostatic rotary encoder configuration 725 that is similar to configuration 700 except that electrostatic shield 730 includes multiple tracks (e.g., see also FIG. 6B) and electrostatic field sensor 715 includes multiple sensor circuits 720 (e.g., one per track).

FIG. 7C is a cross-sectional illustration of an electrostatic rotary encoder configuration 731 that includes a patterned electret unit 735 disposed adjacent to an electrostatic field sensor 715, in accordance with an embodiment of the disclosure. FIG. 7D is a plan view illustration of a demonstrative patterned electret unit 735. Configuration 731 operates by rotating patterned electret unit 735 relative to electrostatic field sensor 715. In other words, either patterned electret unit 735 or electrostatic field sensor 715, or both, may rotate. The individual electret elements 740 form a charge distribution pattern that is sensed by electrostatic field sensor 715. The relative rotation is sensed and tracked as a modulation of the electrostatic field at sensing circuit 720. Electrostatic field sensor 715 is activated by the individual electret elements 740 that generate the charge distribution pattern. Although FIG. 7D illustrates patterned electret unit 735 having just six discrete electret elements 740, it should be appreciated that patterned electret unit 735 may include more or less such elements to increase or decrease angular resolution and may also include a quadrature encoding having multiple tracks of electret elements 740.

FIG. 7E is a cross-sectional illustration of an electrostatic rotary encoder configuration 745 that includes a patterned electrostatic field sensor 750 including multiple instances of a sensing circuit 720 disposed adjacent to an electret unit 755, in accordance with an embodiment of the disclosure. FIG. 7F is a plan view illustration of a demonstrative patterned electrostatic field sensor 750. Configuration 745 operates similar to configuration 731 except replaces multiple electret elements for multiple sensing circuits 720 to increase angular resolution of the modulation of the electrostatic field at the electrostatic field sensor 750. Of course, configurations 731 and 745 may be combined into a single implementation having a pattern electret unit and a pattern electrostatic field sensor working in unison to increase encoding resolution.

Figure 8:
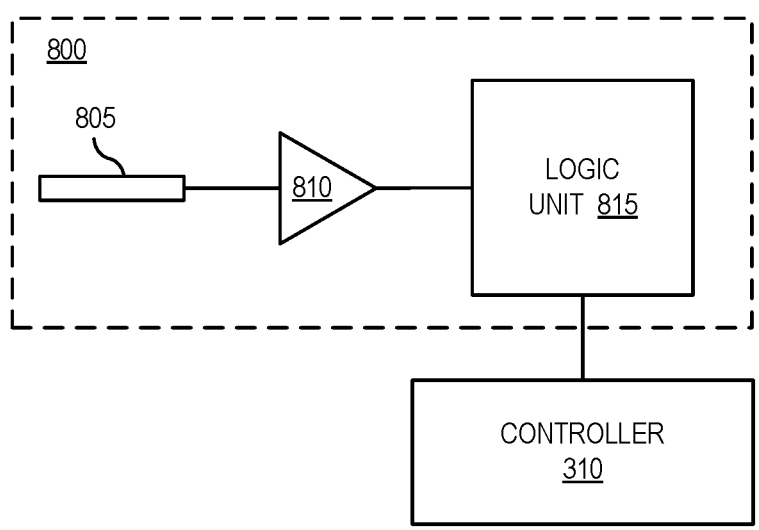
FIG. 8 is a functional block diagram of a sensing circuit for an electrostatic field sensor, in accordance with an embodiment of the disclosure.

FIG. 8 is a functional block diagram of a sensing circuit 800 for an electrostatic field sensor, in accordance with an embodiment of the disclosure. The illustrated embodiment of sensing circuit 800 includes an electrode 805, a charge amplifier 810, and a logic unit 815. Electrode 805 senses the electrostatic field and is coupled to an input of charge amplifier 810. In one embodiment, electrode 805 is a conductive element (e.g., strip, contact pad, etc.). Charge amplifier 810 has a high impedance input that is coupled to sense charge at its input and output an amplified signal. Charge amplifier 810 may be implemented as a trans-impedance amplifier that outputs a voltage signal. For example, charge amplifier 810 may be implemented as a MOSFET having its gate terminal coupled to electrode 805. Logic unit 815 senses the output of charge amplifier 810 and outputs a logic value indicating whether sensing circuit 800 is activated or deactivated in response to a modulated electrostatic field. For example, logic unit 815 may include a voltage comparator and a latch. Other circuit implementations may be possible. The output value indicating activation or deactivation is provided to controller 310 which tracks and encodes the activations into a rotational position of the electrostatic rotary encoder.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A rotary encoder, comprising:
an electret unit to generate an electrostatic field;
an electrostatic field sensor disposed proximate to the electret unit to sense a modulation of the electrostatic field that varies with rotation of one or more rotary components of the rotary encoder about a rotation axis of the rotary encoder;
an electrostatic shield disposed between the electret unit and the electrostatic field sensor, wherein the electrostatic shield includes:
a first shield layer having a first hole pattern; and
a second shield layer having a second hole pattern, wherein the first shield layer rotates relative to the second shield layer forming shutters that periodically open and close with rotation of the first hole pattern relative to the second hole pattern; and
a controller electrically coupled to the electrostatic field sensor to track activations of the electrostatic field sensor as the one or more rotary components rotate, wherein the controller is configured to digitally encode a rotational position of the one or more rotary components based upon the activations.

2. The rotary encoder of claim 1, wherein the electrostatic shield modulates the electrostatic field at the electrostatic field sensor as the one of more rotary components are rotated about the rotation axis.

3. The rotary encoder of claim 2, wherein the one or more rotary components includes the first shield layer which rotates relative to the second shield layer.

4. The rotary encoder of claim 3, wherein the first and second hole patterns each include an inner ring pattern and an outer ring pattern having different periods to provide quadrature encoding of the rotational position of the one or more rotary components.

5. The rotary encoder of claim 1, wherein the one or snore rotary components includes a shaft aligned with the rotation axis to rotate about the rotation axis, wherein the shaft is coupled to drive rotation of the one or more rotary components.

6. The rotary encoder of claim 1, wherein the electret unit comprises a monolithic electret element.

7. The rotary encode of claim 6, wherein the electret unit further comprises a conductive annular substrate with the monolithic electret element suspended within a center of the conductive annular substrate.

8. The rotary encoder of claim 1, wherein the electrostatic field sensor comprises a sensing circuit including:
   an electrode;
   a charge amplifier having an input coupled to the electrode; and
   a logic circuit coupled to an output of the charge amplifier to determine when the electrostatic field sensor is activated by the electrostatic field.

9. The rotary encoder of claim 8, wherein the electrostatic field sensor comprises a plurality of instances of the sensing circuit, and wherein rotation of the instances of the sensing circuit relative to the electret unit modulates the electrostatic field at the electrostatic field sensor.

10. The rotary encoder of claim 1, wherein the electret unit comprises a plurality of electret elements collectively forming a charge distribution pattern, and wherein rotation of the charge distribution pattern relative to the electrostatic field sensor modulates the electrostatic field at the electrostatic field sensor.

11. A drug injection apparatus, comprising:
   a fluid delivery mechanism that translates a linear plunging motion into a rotational motion when dispensing a fluid from a vial;
   a shaft coupled to the fluid delivery mechanism that rotates as the fluid is dispensed; and
   a dosage measurement system for tracking dosages of the fluid dispensed over time, the dosage measurement system including:
      an electret unit to generate an electrostatic field;
      an electrostatic field sensor disposed proximate to the electret unit to sense a modulation of the electrostatic field that varies with rotation of the shaft; and
      a controller electrically coupled to the electrostatic field sensor to track activations of the electrostatic field sensor as the shaft rotates, wherein the controller is configured to digitally encode a rotational position of the shaft based upon the activations.

12. The drug injection apparatus of claim 11, wherein the dosage measurement system further includes:
   an electrostatic shield disposed between the electret unit and the electrostatic field sensor, wherein the electrostatic shield modulates the electrostatic field at the electrostatic field sensor as the shaft rotates.

13. The drug injection apparatus of claim 12, wherein the electrostatic shield comprises:
   a first shield layer having a first hole pattern; and
   a second shield layer having a second hole pattern, wherein the first shield layer is attached to the shaft to rotate relative to the second shield layer forming shutters that periodically open and close rotation of the first hole pattern relative to the second hole pattern.

14. The drug injection apparatus of clam 13, wherein the first and second hole patterns each include an inner ring pattern and an outer ring pattern having different periods to provide quadrature encoding of the rotational position f the shaft.

15. The drug injection apparatus of claim 13, further comprising:
   a support member mounted to the shaft to .ate with the shaft, wherein the electret unit is disposed on the support member and rotates with the shaft, wherein the electret unit is sandwiched between the first shield layer and the support member while the second shield layer is held stationary within the drug injection apparatus.

16. The drug injection apparatus of claim 11, wherein the electret unit comprises a monolithic electret element.

17. The drug injection apparatus of claim 16, wherein the electret unit further comprises a conductive annular substrate with the monolithic electret element suspended within a center of the conductive annular substrate.

18. The drug injection apparatus of claim 11, wherein the electrostatic field sensor comprises a sensing circuit including:
   an electrode;
   a charge amplifier having an input coupled to the electrode; and
   a logic circuit coupled to an output of the charge amplifier to determine when the electrostatic field sensor is activated by the electrostatic field.

19. The drug injection apparatus of claim 18, wherein the electrostatic field sensor comprises a plurality of instances of the sensing circuit disposed at different offset angles about a rotation axis of the shaft and coupled to rotate with the shaft, and wherein rotation of the instances of the sensing circuit relative to the electret, unit modulates the electrostatic field at the electrostatic field sensor.

20. The drug injection apparatus of claim 11, wherein the electret unit comprises a plurality of electret elements collectively forming a charge distribution pattern coupled to rotate with the shaft, wherein rotation of the charge distribution pattern relative to the electrostatic field sensor modulates the electrostatic field at the electrostatic field sensor.

21. A rotary encoder, comprising:
   an electret unit to generate an electrostatic field, wherein the electret unit comprises a monolithic electret element having a uniform charge distribution;
   an electrostatic field sensor disposed proximate to the electret unit to sense a modulation of the electrostatic field that varies with rotation of one or more rotary components of the rotary encoder about a rotation axis of the rotary encoder; and
   a controller electrically coupled to the electrostatic field sensor to track activations of the electrostatic field sensor as the one or more rotary components rotate, wherein the controller is configured to digitally encode a rotational position of the one or more rotary components based upon the activations.

22. The rotary- encoder of claim 21, further comprising:
   an electrostatic shield disposed between the electret unit and the electrostatic field sensor, wherein the electrostatic shield modulates the electrostatic field at the electrostatic field sensor as the one or more rotary components are rotated about the rotation axis.

* * * * *

UNITED STATES PATENT AND TRADEMARK OFFICE
CERTIFICATE OF CORRECTION

PATENT NO. : 11,185,636 B2
APPLICATION NO. : 16/513618
DATED : November 30, 2021
INVENTOR(S) : R. Mirov et al.

It is certified that error appears in the above-identified patent and that said Letters Patent is hereby corrected as shown below:

In the Claims

| Column | Line | |
|---|---|---|
| 9 | 6 | in Claim 5, change "snore" to -- more --. |
| 9 | 13 | in Claim 7, change "encode" to -- encoder --. |
| 10 | 10 | in Claim 15, change ".ate" to -- rotate --. |
| 10 | 36 | in Claim 19, change "electret," to -- electret --. |
| 10 | 59 | in Claim 22, change "rotary- encoder" to -- rotary encoder --. |

Signed and Sealed this
Twenty-first Day of February, 2023

Katherine Kelly Vidal
*Director of the United States Patent and Trademark Office*